(12) United States Patent
Lipps et al.

(10) Patent No.: US 6,936,423 B1
(45) Date of Patent: Aug. 30, 2005

(54) ANTI-LTNF FOR IN VITRO ASSAY OF BIOLOGICAL TOXINS

(76) Inventors: Binie V. Lipps, 4509 Mimosa Dr., Bellaire, TX (US) 77401; Frederick W. Lipps, 4509 Mimosa Dr., Bellaire, TX (US) 77401

( * ) Notice: Subject to any disclaimer, the term of this patent is extended or adjusted under 35 U.S.C. 154(b) by 0 days.

(21) Appl. No.: 09/300,612

(22) Filed: Apr. 27, 1999

(51) Int. Cl.[7] .................... G01N 33/53; G01N 33/569; A61K 38/10; C07K 14/47; C07K 7/08
(52) U.S. Cl. .................. 435/7.1; 435/7.3; 435/7.72; 435/7.94; 435/7.95; 435/7.9; 514/8; 514/12; 514/14; 514/21; 530/300; 530/326; 530/350; 530/362; 530/380; 530/388.1; 530/416; 530/829; 530/830
(58) Field of Search ................. 530/380, 386, 530/387.1, 388.1, 300, 326, 350, 362, 416, 829, 830; 514/14, 8, 12, 21; 435/7.1, 7.72, 7.94, 7.95, 7.9

(56) References Cited

U.S. PATENT DOCUMENTS 5,576,297 A * 11/1996 Lipps et al. .................. 514/14
5,744,449 A * 4/1998 Lipps et al. .................. 514/14

OTHER PUBLICATIONS

Harlow and Lane; Antibodies: A Laboratory Manual; Chapter on Monoclonal Antibodies and Immunoassays;Especially pp. 148–150,247 and 579, 1988.*
Sanchez et al 1998, Toxicon: 36: 1451–1459.*
Harlow and Lane 1988, chapter 14, mmunoassays, pp. 579, 585 and 563).*
Farah et al 1996, Toxicon: 34: 1067–1071.*
Chu F.S. and Fan T.S.L. (1985) Indirect Enzyme–Linked Immunosorbent Assay for Saxitoxin in Shellfish. J. Ass. Off. Analyt. Chem. 68:13–16.
Hatheway C.L. and Ferreira J.L. (1996) Detection and Identification of *Clostridium Botulinum* Neurotoxins in Natural Toxins. p 481–498. (Singh B L & Tu A T eds.) Plenum Press.
Horowitz W (ed) (1990) Official Method of Analysis, Wash. DC, Assoc of Official Analytical Chemists p 881–882.
Leith A.G., Griffiths, G.D. and Green M A (1988) Quantitations of Ricin Toxin using a Highly Sensitive Avidin/Biotin Enzyme–Linked Immunosorbent Assay J. Forensic Sci. Soc. 28: 227–236.

Li, Q. and Ownby, C.L. (1994) Development of an Enzyme–Linked Immunosorbent Assay ELISA for Identification of Venoms From Snakes in *Agkistrodon* Genus.
Morton S. L. and Tindall D. R. (1996) Determination of Okadaic Acid Content of Diniflagellate Cells A Comparison of the HPLC–Fluorescent Method and Two Monoclonal Antibody ELISA kits. Toxicon 34: 947–954.
Poli, M.A., Rivera V.R, Heweston J.F. and Merrill (1994) Detection of Ricin by Colorimetric and Chemiluminecence ELISA, Toxicon 32: 1371–.
Potter M. D., Meng J. and Kimsey P. (1993) An ELISA Test for Detectors of Botulinum Toxin Types A, B and E in Innoculated Food Samples. J. Food Prot. 56:856–861.
Sommer H. and Meyer, K. F. (1937) Paralytic Shell–Fish Poisoning. Arch Path 24: 560–598.

* cited by examiner

*Primary Examiner*—L. F. Smith
*Assistant Examiner*—Padma Baskar
(74) *Attorney, Agent, or Firm*—John R Casperson

(57) ABSTRACT

Lethal Toxin Neutralizing Factor has been isolated in purity from opossum serum by high pressure liquid chromatography (HPLC) fractionation. The amino acid sequence from the N-terminal for the first fifteen amino acids of LTNF-n is: Leu Lys Ala Met Asp Pro Thr Pro Pro Leu Trp Ile Lys Thr Glu. Antibodies to LTNF-n and synthetic peptides consisting of fifteen, ten and five amino acids from the N-terminal of the above sequence, designated as LTNF-15, LTNF-10 and LTNF-5 were produced by immunizing Balb/C mice to produce Anti-LTNF-n, Anti-LTNF-15, Anti-LTNF-10 and Anti-LTNF-5. The anti LTNF-n, anti-LTNF-15, anti-LTNF-10 and anti-LTNF-5 react immunologically with all types of toxins derived from animal, plant and bacteria and can be assayed by immunological in vitro test such as ELISA tests. Anti-LTNFs react roughly proportional to lethal dose of biological toxins under in vitro immunological ELISA test similar to the mouse bioassay test. This property of anti-LTNFs can be utilized to replace the use of animals for bioassay of toxins from animal, plant and bacteria. Anti-LTNFs can be polyclonal raised in animals or monoclonal made in hybridomas. Anti-LTNFs can be used in crude form for immunological in vitro testing. However, purified IgG from the anti LTNFs is most desirable for consistent results from the in vitro tests. In general, the in vitro use of Anti-LTNFs is a replacement for animal use as is currently required for the assay of biological toxins.

7 Claims, No Drawings

SEQUENCE LISTING (1) GENERAL INFORMATION:

(iii) NUMBER OF SEQUENCES:   1

(2) INFORMATION FOR SEQ ID NO:   1:

(i) SEQUENCE CHARACTERISTICS:
      (A) LENGTH:   15
      (B) TYPE:      AMINO ACID
      (C) STRANDEDNESS: SINGLE
      (D) TOPOLOGY:   LINEAR (ii) MOLECULE TYPE: PROTEIN IN SEQ ID NO: 1

(iii) HYPOTHETICAL: NO (iv) ANTI-SENSE:

(v) FRAGMENT TYPE:

(vi) ORIGINAL SOURCE: OPOSSUM SERA: SEQ ID NO: 1:
      (A) ORGANISM: DIDELPHIS VIRGINIANA
      (B) STRAIN:   WILD
      (C) INDIVIDUAL ISOLATE:   TEXAS WILD
      (D) DEVELOPMENTAL STAGE: ADULT
      (E) HAPLOTYPE:
      (F) TISSUE TYPE: BLOOD
      (G) CELL TYPE:
      (H) CELL LINE:
      (I ) ORGANELLE:

(vii) SEQUENCE DESCRIPTION: SEQ ID NO: 1:

Leu Lys Ala Met Asp Pro Thr Pro Pro Leu Trp Ile Lys Thr Glu
1         5                 10             15

ANTI-LTNF FOR IN VITRO ASSAY OF BIOLOGICAL TOXINS

BACKGROUND OF THE INVENTION

The invention relates to the introduction of a novel reagent for estimating biological toxins by in vitro test, as a replacement of currently used animal bioassay.

The direct testing of the toxins on animals poses ethical and moral questions. Therefore, there is great need for an alternative assay for biological toxins as a replacement for animal testing.

Biological toxins are grouped according to the source, such as: animal, plant, unicellular or one celled algae, and bacteria. Toxins are diverse and range from well-defined single macromolecules (*tetanus, diphtheria*, and *botulinum* toxins) to mixtures of complex molecules such as: snake or scorpion venoms or simple chemical entities (digitoxin, colchicine, tricyclic anti-depressants).

Mouse bioassay is the accepted and practiced method for assaying toxins, and is recommended by the Association of Official Analytical Chemists (AOAC). However, the mouse test for biological toxins is expensive and is disliked by animal activists and pressure is mounting worldwide to eliminate live animal bioassays. Germany, Switzerland and Australia have already banned the use of mammals for venom lethality tests.

The mouse bioassay suffers from other shortcomings as well. Toxins not lethal to mouse will go undetected by mouse bioassay. Also, mouse bioassay collectively detects the lethal effects of toxin, whether it is a single toxin or a mixture of several toxins.

Numerous investigators have developed immunological tests for assaying various toxins. Immunological tests are based on the principle of antigen-antibody reaction. Polyclonal antibodies are raised by immunizing animals: mouse, rabbit, rat, goat, etc. with a toxin.

Monoclonal antibodies are prepared in hybrid-oma cells. Spleen cells from an animal immunized with desired toxin are fused with corresponding species of myeloma cells. Both monoclonal and polyclonal antibodies produced are specific to the toxin (antigen used for immunization), and react with specific toxin.

The most frequently used in vitro immunological test is Enzyme Linked Immunosorbent Assay (ELISA). Biological toxins are assayed by several types of ELISA tests using specific antibodies to the desired toxin. ELISA tests can be carried out with numerous variations, although the most common format for detecting toxin from serum samples is the antigen-capturing method also known as double-sandwich method.

Li and Ownby reported the development of ELISA test for identification of venoms from snakes in the Agkistrodon genus. Several investigators have reported the development of ELISA for different toxins such as ricin and botulinum toxins; types A, B, and E in inoculated food samples. Morton and Tindall compared three tests; HPLC fluorescent method and two monoclonal antibody test kits for the determination of okadaic acid content of dinoflagellate cells and the results were not consistent. Since outbreaks of diuretic shellfish poisoning (DSP) may be caused by okadaic acid, methylokadaic acid, or a combination of these toxins, they concluded that both kinds of ELISA kits may underestimate total toxin effect in toxic shellfish.

All these methods suffer disadvantages, which have prevented their wide spread implementation particularly under the regulatory requirements. The mouse bioassay detects a wide range of known and presumably unknown toxins. Therefore, it is unlikely that it will be abandoned completely in favor of existing bioassays, until an alternative is found which is similarly responsive.

What is needed is a reagent that can be used in a common protocol for an in vitro assay test for biological toxins.

What is further needed is an in vitro test that can recognize all types of toxins, as a replacement of animal use.

OBJECTS OF THE INVENTION

An object of the present invention is to provide a novel reagent, specifically, Anti Lethal Toxin Neutralizing Factor (anti-LTNF), having a property to bind to all types of toxins derived from animal, plant and bacteria and can be assayed by immunological in vitro test, specifically, ELISA.

Another object of the invention is to provide a method to use Anti-LTNF having such a unique property to recognize all types of toxins in vitro test with sensitivity greater than in vivo mouse test.

Another object of the invention is to provide anti-LTNFs (made versus natural and synthetic LTNF) for use in a simple, cheap, ethically accepted in vitro alternative as a replacement for the currently used animal bioassay.

Another object of the invention is to provide a method of identifying toxins by an ELISA sandwich utilizing anti-LTNF as primary antibody and a set of secondary antibodies specific to the known toxins selected for the test.

SUMMARY OF THE INVENTION

In one embodiment of the invention, there is provided the novel composition of matter, anti-LTNF. Anti-LTNF is the antibody produced biologically in response to natural Lethal Toxin neutralizing Factor (LTNF-n) or LTNF-s the synthetic active domain from LTNF-n. These materials are generically referred to herein as LTNFs. LTNF-n is a protein isolated from opossum serum having a molecular weight of 68 kDa and the amino acid sequence from the N-terminal of Leu Lys Ala Met Asp Pro Thr Pro Pro Leu Trp Ile Lys Thr Glu. LTNF-s is a synthetic fragment of LTNF-n consisting of the portion of the N-terminal sequence of LTNF-n. A highly desirable active species of anti-LTNF is produced biologically in response to an LTNF-s having the first ten amino acids of the above sequence.

In another embodiment of the invention, an unknown toxin in fluid state is brought together with an anti-LTNF. The resulting immunological reaction indicates the presence of toxin in the fluid. The immunological reaction can determine the potency of the toxin.

Because anti-LTNF immunologically binds to all types of toxins, it can be used in vitro to test toxicity or to test for the presence of toxins as an alternative to animal testing. It can also be used for the identification of toxins by reacting with specific antitoxins under investigation.

DETAILED DESCRIPTION OF THE INVENTION

Anti-LTNF is the antibody made versus LTNF-n and anti-LTNF-s is made versus LTNF-s.

As used herein, LTNF-n refers to natural LTNF isolated from opossum serum having a molecular weight of about 68 kDa. The amino acid sequence (AA) from the N-terminal for the first fifteen amino acids of LTNF-n is:

Leu Lys Ala Met Asp Pro Thr Pro Pro Leu Trp Ile Lys Thr Glu.

For additional details, see U.S. Pat. No. 5,744,449, the disclosure of which is incorporated by reference.

The synthetic LTNF comprising of 15 amino acids was identified as the active domain of the LTNF-n.

Synthetic LTNF or LTNF-s refers to a synthetic peptide having a molecular weight of less than 2,500 and at least a portion of the sequence set forth above. Preferably, LTNF-s has at least a 3-amino acid portion of the sequence, more preferably, at least a 5 amino acid portion of the sequence, and most preferably, at least a 7 amino acid portion of the sequence. Specific examples of LTNF-s include LTNF-15, LTNF-10 and LTNF-5. LTNF-15 is the 15 amino acid peptide having the first 15 amino acids of the above sequence and a molecular weight of 1,989 daltons. LTNF-10 is the 10 amino acid peptide having the first ten amino acids of above sequence with molecular weight of 1242 daltons. LTNF-5 is the 5 amino acid peptide having the first five amino acids of the above sequence with molecular weight of 647 daltons.

PRODUCTION OF ANTI-LTNF

Antibodies in general, are produced in animals by injecting the desired protein, which makes specific circulating antibodies to the protein. The serum of the immunized animal reacts immunologically to the protein, which was used for immunization. The presence of antibodies to the protein can be detected by various in vitro tests such as ELISA and immunoprecipitin test (IP).

LTNF-n and synthetic peptides consisting of fifteen, ten and five amino acids, designated as LTNF-15, LTNF-10 and LTNF-5 were used to produce antibodies by immunizing Balb/C mice. The sera of the immunized mice contained specific antibodies. In other words, mice immunized with LTNF-n produced antibodies specific to LTNF-n, anti LTNF-n is formed. Likewise, mice immunized with synthetic peptides LTNF-15, LTNF-10 and LTNF-5 produced anti-LTNF-15, anti-LTNF-10 and anti-LTNF-5 respectively.

(1) Polyvalent anti-LTNFs can be made in animals, mice, rabbits, goats etc. (2) monoclonal anti-LTNFs can be made in fused hybridoma cells secreting antibodies (3) or anti-LTNFs can be made in ascitic cavities of mice by injecting hybridoma antibody secreting cells.

There is a perception that small synthetic peptides do not generate antibodies on injection into animals. However, synthetic peptide can generate antibodies if it is tagged with a complete protein, before injecting to the animal. Landsteiner coined the term hapten for a low molecular weight, chemically defined compound which could induce antibody formation only when coupled to a larger carrier protein molecule, before injecting. Thereby, the injected animal makes antibodies to both the hapten and the carrier protein.

Synthetic chemically defined LTNFs comprising of fifteen, ten and five amino acids can be considered as haptens and therefore, theoretically should not induce antibodies if injected without carrier protein. However, surprisingly, synthetic LTNF consisting of fifteen amino acids was able to induce antibodies on injecting in mice. Encouraged by these results, mice were injected with synthetic LTNFs consisting of ten and five amino acids to induce antibodies, in a similar protocol. Each synthetic LTNF consisting of fifteen, ten and five amino acids was able to induce specific antibodies as assayed by ELISA and IP.

SEPARATION OF ANTI-LTNF IgG

Purification of IgG from Mouse anti-LTNFs:

Purification of immunoglobulin (IgG) can be accomplished by various methods and one of them is by high pressure liquid chromatography (HPLC). Anti sera were fractionated on HPLC from Tosoh Co. (Japan) using ionic exchange column from Polymer Laboratories (UK) and Trizma-HCl gradient buffer pH 7.4. For a run, 20 mg of serum protein containing desired antibody was loaded for fractionation. The IgG fraction was collected dialyzed and concentrated using apparatus from Spectrum Co. The concentrated fraction of IgG was refractionated on HPLC under identical conditions to obtain homogeneous preparation of IgG.

USES OF ANTI-LTNFs

Anti-LTNFs can be used to assay the toxicity of venom or venom toxins.

Anti-LTNFs can be used to assay the toxicity of toxins from sources other than venoms.

Anti-LTNFs can be used to detect the presence of multiple unrelated toxins.

Anti-LTNFs can be used to detect the presence of toxins in foods or biological fluids such as blood serum, saliva, urine, milk, tears etc.

Anti-LTNFs can be used to determine the potency of antivenoms and antitoxins.

The unique property of anti-LTNF to bind to all tested types of toxins immunologically in a fashion comparable to animal bioassay, is the theme of this patent.

The protein LTNF-n and the synthetic peptides LTNF-15, LTNF-10 and LTNF-5 do not react immunologically with toxins by ELISA or IP tests. However, the anti-LTNFn, anti LTNF-15, anti LTNF-10 and anti LTNF-5 react immunologically with all tested toxins, as revealed by ELISA and IP tests. Moreover, the binding affinity of anti-LTNFn and the anti-synthetic LTNF-15, LTNF-10 and LTNF-5 roughly proportional to the lethal dose of the toxin under testing.

Using the novel reagent anti-LTNF, ELISA tests can be performed in several different ways: Furthermore, anti-LTNFs can be used in crude form as anti serum, or it's purified IgG. However, to avoid background purified, it is ideal to use IgG for ELISA tests.

ELISA tests for assaying toxins can be performed by using different concentrations of toxins and reacting with constant amount of purified IgG from anti-LTNF.

ELISA Method in Antigen Capture Format:

ELISA can be done in antigen capture format (also called double sandwich) where anti-LTNF IgG from one species (mouse) is used to capture the toxin and anti-LTNF from another species (rabbit) is used to recognize the toxin. For commercialization, two types of antibodies either polyclonal or monoclonal, to LTNFs, natural, or synthetic, should be used. One for capturing the toxin and other for conjugating with alkaline phosphotase or peroxidase to recognize the toxin as in the antigen capture format.

Toxin detection from foods, sera or other body fluids must be done by antigen capture format. The second antibody can be conjugated directly to alkaline phosphatase or horse radish peroxidase to eliminate one step of washing the plate and to save one-hour incubation period. IgGs from all four anti-LTNFs to: LTNF-n, LTNF-15, LTNF-10 and LTNF-5 were tested in ELISA immunological tests and were found equally good.

EXAMPLES

Example I

Production of Polyclonal Antibodies

Production of Polyclonal Antibodies to LTNFs (LTNF-15, LTNF-10 and LTNF-5): Adult Balb/C mice were used for immunization. The mice were used in compliance with the U.S. Public Health Service policy on humane care and use of animals. For the first injection each type of LTNF was mixed with equal amount of Freund's complete adjuvant and for the subsequent doses, the antigens were mixed with incomplete Freund's adjuvant. The mice were injected intra muscularly with 100 μg/mouse, four to six times, two weeks apart. At the end of the immunization period, mice were bled through ophthalmic vein and sera were separated.

Enzyme-Linked Immunosorbent Assay (ELISA) for Cross Reactivity of Anti-LTNFs:

ELISA tests were performed in 96 well microtiter plate. The plate was coated with one concentration of antigen. The wells of the plate were filled with 10 μg/ml in 0.05 M phosphate buffered saline (PBS) pH 7.3 and 100 μl/well, for each type of LTNFs such as natural LTNF (LTNF-n), synthetic peptide consisting of 15 amino acids (LTNF-15), consisting of 10 amino acids (LTNF-10) and consisting of 5 amino acids (LTNF-5). The plate was incubated for overnight at room temperature. After 18 to 24 hours the plate was washed three times (3X) with PBS and the plate was blocked with 0.25 ml/well of 3% Teleostean gelatin from cold water fish (Sigma) for ½ hour at RT.

Mouse anti-LTNFn, anti-LTNF-15, anti-LTNF-10 and anti-LTNF-5 diluted three fold were added to the coated plate and the plate was incubated at 37° C. for 1 to 2 hours. The plate was washed 3X with PBS and horseradish peroxidase conjugated with mouse IgG made in goat (Sigma) was added and incubated for 1 hour at 37° C.

After which the plate was washed 3X with PBS and reacted with O Phenylenediamine Dihydrochloride (OPD) for color development. The test was read after ½ hour visually or preferably on ELISA plate reader. The results are presented in table 1.

Immunoprecipitation Test (IP):

IP was carried out as described by Ouchteriony. Agarose in 1-% concentration was dissolved by heating in normal saline and 7 ml of it was placed in 35-mm diameter petri dish. After the hardening of agarose, five wells were punched, one in the center and four peripheral wells, 1.0 cm apart from the central well. The central well was filled with one type of undiluted anti serum and the peripheral with four LTNFs having concentration 5 mg/ml. The wells were filled several times 50 μl each time, over the period of 72 hours. The results are presented in table 1.

TABLE 1

Immunological Cross Reactivity of Natural and Synthetic LTNFs by ELISA and by IP.

| Antigen | ELISA titer | | | | Immuno. Precipitation | | | |
|---|---|---|---|---|---|---|---|---|
| | Anti LTNF | Anti LT15 | Anti LT10 | Anti LT5 | Anti LTNF | Anti LT15 | Anti LT10 | Anti LT5 |
| Nat-LTNF | 24300 | 600 | 2700 | 900 | + | + | + | + |
| Syn-LTNF-15 | 8100 | 2700 | 2700 | 900 | + | + | + | − |
| Syn-LTNF-10 | 8100 | 8100 | 8100 | 900 | − | − | + | − |
| Syn-LTNF-5 | 8100 | 900 | 2700 | 600 | − | − | + | − |

The results of table 1 show that synthetic peptides consisting of as small as five amino acids are capable of producing antibodies in mice. The antibodies versus LTNF-15, LTNF-10 and LTNF-5 cross react with each other and with the natural LTNF-n by ELISA and by IP. Among the three, anti-LTNF-10 proves to be better than anti-LTNF-15 and anti-LTNF-5.

It appears that the active domain of LTNF-n resides in ten amino acids. Therefore, LT-10 produced antibodies having high potency immunologically. LT-15 is may be too long having five amino acids not necessary for the active domain and LT-5 is too short of five amino acids, to generate antibodies having similar immunological potency.

Example II

Immunological Reaction of Anti-LTNF with Venom Toxin

Immunological Binding of Anti-LTNF to Venoms by ELISA:

The lethal dose was determined by injecting intraperitoneally 0.1 ml of venom in various concentrations in 20 g ICR mice. ELISA test was carried in 96 well microplate. The wells of the microplate were coated with 0.1 ml of various concentrations of venom as antigen starting from 100 μg to 0.000564 (564 nanogram) diluted threefold in 0.05 M phosphate buffer saline pH 7.4 (PBS) and incubated for overnight at room temperature. After 18 to 24 hours the plate was washed three times (3X) with PBS and the plate was blocked with 0.25 ml/well of 3% Teleostean gelatin from cold water fish (Sigma) for ½ hour at RT. The plate was washed 3X with PBS and 0.1 ml/well of 10 μg/ml purified mouse anti-LTNF IgG was added. The plate was incubated at 37° C. for 1 to 2 hours. And then, the plate was washed 3X with PBS and horseradish peroxidase conjugated with mouse IgG made in goat was added and incubated for 1 hour at 37° C. After which the plate was washed 3X with PBS and reacted with O Phenylenediamine Dihydrochloride (OPD) for color development. The test was read after ½ hour visually or preferably on ELISA plate reader. The results are shown in table 2.

TABLE 2

Immunological binding of anti-LTNF-n to venoms.

| Venom | Lethal dose μg | ELISA dose μg | Ratio L/E |
|---|---|---|---|
| Crotalus atrox. (Rattlesnake) | 300 | 3.7 | 81 |
| Naja n. kaouthia (Thailand cobra) | 35 | 0.1 | 350 |
| Vipera russelli (Common viper) | 90 | 0.4 | 225 |
| Oxyuranus scutellatus (Australian taipan) | 3.5 | 0.02 | 175 |
| Androctonus australis (Scorpion) | 15 | 0.2 | 75 |
| Astrotia stokesii (Sea snake) | 4.0 | 0.03 | 133 |

The results of table 2 show that the toxicity of venoms was roughly proportional to the ELISA binding or ELISA titer. The mouse lethal dose for C. atrox venom was 300 μg and ELISA was 3.7 μg. Mouse lethal dose for sea snake Astrotia stokesii was 4 μg and its ELISA was 0.03 μg.

Example III

Toxicity is Proportional to Binding Affinity with Toxins as well

Mouse Lethality of Toxins and Binding Affinity to Anti-LTNF IgG by ELISA:

The lethal dose was determined by injecting intraperitoneally 0.1 ml of toxin at various concentrations in 20 g ICR mice. ELISA test was performed as described above using three fold concentrations of toxin and 10 μg/ml anti-LTNF IgG. Results are shown in table 3.

TABLE 3

Mouse lethality of toxins in micro grams and
binding affinity to anti-LTNF IgG by ELISA

| Toxin | Source | Lethal dose μg | ELISA dose μg | Ratio L/E |
|---|---|---|---|---|
| BoTx | Clostridium botulinum | 1 | 0.04 | 25 |
| Cholera | Cholerae vibrio | ND* | 0.11 | |
| Cobratoxin | Naja n. kaouthia | 3 | 0.2 | 15 |
| Crotoxin | Crotalus d. terrificus | 5 | 1.1 | 4.5 |
| Holothurin | Actinopyga agrassizi | 200 | 1.8 | 111 |
| Ricin | Ricinus communis | 2 | 0.04 | 50 |
| Taipoxin | Oxyuranus scutellatus | 5 | 1.1 | 4.5 |
| Toxic shock | Staphylococeus aureus | ND* | 0.33 | |

*ND = not determined because these toxins are not lethal to adult mice.

The results of table 3 show that lethality of toxins is roughly proportional to the ELISA binding or ELISA titer. Mouse lethal dose for BoTx (*botulinum* toxin) was 1 μg and ELISA detection level was found to be 0.04 μg, whereas, for Holothurin mouse lethal dose was 200 μg and its detection level by anti-LTNF was 1.8 μg. Lower the ELISA binding means higher the detection level.

Example IV

Multiple Toxins can be Detected
Anti-LTNFs Detect the Presence of Multiple Unrelated Toxins:

Equal volumes of ricin at 10 μg/ml was mixed with equal concentration of different toxins; BoTx, *Cholera* toxin and *Staphylococcus aureus* toxin. ELISA tests were carried using individual toxin and ricin plus other toxin as antigens. The toxins individually and the mixtures were diluted three fold. The binding was assayed by IgGs from anti-ricin and anti-LTNF. The results are shown in table 4.

TABLE 4

Anti-LTNFs detect presence of several unrelated toxins

| | Binding affinity, μg | |
|---|---|---|
| Toxin | Anti-Ricin | Anti-LTNF |
| Ricin | 330 | 400 |
| Ricin + BoTx | 330 | 370 |
| BoTx | 0 | 37 |
| Ricin + Cholera | 330 | 110 |
| Cholera | 0 | 37 |
| Ricin + Sta. aureus | 330 | 12.3 |
| Toxic shock | 0 | 45 |

The results clearly show that anti-ricin detects only ricin by classical specific antigen-antibody reaction and non-of the other toxins mixed with it. However, anti-LTNF detects the presence of ricin as well as other toxins; BoTx, *Cholera* and *Sta. aureus*. Thus, anti-LTNF has the unique property of binding with all tested types of unrelated biological toxins, individually or in mixture.

Example V

Toxins in Food or Animal Body Fluids can be Detected

ELISA Test for Detection of Toxins from Foods by Anti-LTNF:

Human serum, human urine, chicken broth and dairy milk were spiked with 10 μ/ml of different toxins; BoTx, Ricin, *Cholera* and *Sta. aureus*. ELISA test was carried as described previously, using anti-LTNF IgG. The results are seen in table 5.

TABLE 5

Anti-LTNF detects toxins from foods and body fluids

| | Detection Level in nanogram | | | |
|---|---|---|---|---|
| Diluent | BoTx | Ricin | Cholera | Sta. Aureus |
| PBS | 333 | 333 | 111 | 333 |
| Serum | 11 | 11 | 11 | 11 |
| Milk | 220 | 110 | 111 | 111 |
| Broth | 330 | 110 | 111 | 111 |
| Urine | 330 | 220 | 12.3 | 37 |

BoTx: Botulium toxin from *Clostridium botulinum*.
Ricin: Plant toxin from Castor seeds.
Cholera: Toxin from *Vibrio cholerae*.
Sta. aureus: Toxin from *Staphylococcus aureus*.

The detection levels of BoTx, ricin, cholera and toxic shock was the lowest in human serum—down to 11 ng (This corresponds to the highest sensitivity). Detection levels in milk were higher than observed in broth and urine (except for BoTx). The detection levels for *cholera* and *Sta. aureus* were lower in urine than in milk and broth.

Note: The concentrations of serum, milk, broth and urine diluted threefold in PBS for the obtained detection levels without added toxins were ELISA negative. In other words the positive reaction was not due to the protein present in diluent but due to the presence of added toxin. Thus, anti-LTNFs are useful for in vitro assaying various types of food poisoning toxins from liquid and solid foods.

Example VI

Antivenom and Antitoxin Potency can be Determined

Neutralization Assay of Anti-venoms Using Anti-LTNF:

Currently, potency of antivenoms and anti toxins is measured by neutralization tests in mice. Neutralization test requires numerous mice because this test requires a determination of the $LD_{50}$ of venom alone and for the venom neutralized by the antiserum. At least four different concentrations of venom alone and a similar number or more for the venom to be neutralized by the antivenom must be used. In order to achieve statistical significance five to six mice are used per concentration. Thus, to determine the potency of a single antivenom fifty mice are required. (This is undesirable.)

The protein concentration of each venom was adjusted to 200 μg/ml. Each venom was mixed with equal amount of normal rabbit serum and homologous respective rabbit anti serum. The mixtures were incubated at 37° C. for one hour. The mixtures of venom with normal serum and specific anti serum were considered as antigens for ELISA. ELISA test was performed as described above. The results of detection levels of venom toxins in the mixtures are shown in table 6.

TABLE 6

Neutralization assay of venoms using anti-LTNF

| Venom | Binding to anti-LTNF μg | Neutralization Index |
|---|---|---|
| Crotalus atrox + NS | 3.7 | 2.5 |
| Crotalus atrox + anti serum | 1.2 | |
| Naja. n. kaouthia + NS | 1.2 | 1.16 |
| Naja. n. kaouthia + anti serum | 0.04 | |
| V. russelli + NS | 3.7 | 2.9 |
| V. russelli + anti serum | 0.8 | |

TABLE 6-continued

Neutralization assay of venoms using anti-LTNF

| Venom | Binding to anti-LTNF μg | Neutralization Index |
|---|---|---|
| O. scutellatus + NS | 0.8 | 0.6 |
| O. scutellatus + anti serum | 0.2 | |

NS = normal rabbit serum

The results of table 6 show that the detection level or the binding of C. atrox venom was 3.7 μg in normal rabbit serum but dropped to 1.2 μg in presence of homologous rabbit anti C. atrox serum. Thus, showing the difference of 2.5, which is the neutralizing index for this antiserum. The venom neutralized by the specific anti venom is not detected by anti-LTNF. The neutralizing index depends upon the potency of the anti serum. The neutralizing index for anti serum to V. russelli was 2.9 and for O. scutellatus 0.6.

We claim:

1. A process for detecting a toxin in a biological sample, said process comprising (a) contacting a biological sample with an antibody made against a synthetic peptide consisting of at least five consecutive amino acid portion of SEQ ID NO: 1, or
against a natural 68 kDa Lethal Toxin Neutralizing Factor protein, wherein said protein is isolated from opossum serum, and (b) detecting the immune complex formed between the toxin and the antibodies by an ELISA, wherein said sample is obtained from the group consisting of animal, plant and bacteria.

2. A process as in claim 1 wherein said antibodies are in a fluid state and the toxin is attached to a plate, wherein said toxin detected by ELISA is roughly proportional to the lethal dose of the toxin as determined by animal bioassay.

3. A process as in claim 1 wherein the biological sample is selected from the group consisting of food, blood sera, saliva, urine and milk, and the ELISA is carried out by antigen capture format.

4. A method for assaying a free toxin in a sample, said method comprising (a) contacting a sample with an antibody made
against a synthetic peptide consisting of at least five consecutive amino acid portion of
SEQ ID NO: 1, or against a natural 68 kDa Lethal Toxin Neutralizing Factor protein, wherein said protein is isolated from opossum serum, and (b) detecting an immune complex formed between the free toxin in the sample and the antibodies, by an ELISA, wherein said sample is a mixture of a predetermined amount of the toxin and a predetermined amount of the specific anti-serum to said toxin, wherein said mixture contains a reduced amount of free toxin due to partial neutralization by specific anti-serum.

5. A method as in claim 4 wherein the specific anti-serum is made against a venom.

6. A process as in claim 1, wherein said antibodies react immunologically with a wide range of biological toxins.

7. A process as in claim 1 wherein said ELISA is carried out according to an ELISA double-sandwich method protocol.

* * * * *